United States Patent [19]
Irita et al.

[11] Patent Number: 6,003,419
[45] Date of Patent: Dec. 21, 1999

[54] MICROCUTTING DEVICE AND INCISING METHOD

[75] Inventors: Takeshi Irita; Shinya Hara, both of Tokyo; Yoshihiko Suzuki, Chiba, all of Japan

[73] Assignee: Nikon Corporation, Tokyo, Japan

[21] Appl. No.: 09/031,348

[22] Filed: Feb. 27, 1998

[30] Foreign Application Priority Data

| Feb. 28, 1997 | [JP] | Japan | 9-045636 |
| Jul. 9, 1997 | [JP] | Japan | 9-199289 |

[51] Int. Cl.⁶ .................. B26D 1/00; B26D 7/10
[52] U.S. Cl. .................. 83/171; 83/915.5; 83/13; 606/29
[58] Field of Search .............. 83/170, 171, 856, 83/915; 606/29

[56] References Cited

U.S. PATENT DOCUMENTS

| 3,834,265 | 9/1974 | Tafapolsky et al. | 83/915.5 |
| 3,937,564 | 2/1976 | Persson | 83/915.5 |
| 4,532,838 | 8/1985 | Soderkvist | 83/915.5 |
| 4,581,969 | 4/1986 | Kim | 83/915.5 |
| 4,697,489 | 10/1987 | Kim | 83/915.5 |
| 5,299,481 | 4/1994 | Lihl et al. | 83/170 |
| 5,308,311 | 5/1994 | Eggers | 83/171 |

FOREIGN PATENT DOCUMENTS

| 0111291 | 6/1984 | European Pat. Off. | 83/915.5 |
| 0061931 | 4/1982 | Japan | 93/915.5 |
| 8-85018 | 4/1996 | Japan . | |
| 8200890 | 3/1982 | WIPO | 83/915.5 |

*Primary Examiner*—M. Rachuba
*Attorney, Agent, or Firm*—Foley & Lardner

[57] ABSTRACT

A microcutting device incises minute samples of organisms, such as egg cells and protozoa, and the like. This device is made of a thin film plate which is formed by use of a semiconductor manufacturing technique, and has a heater in the vicinity of its cutting edge. The microcutting device is sharper than a metal-blade incision device and is suitable of mass production.

13 Claims, 13 Drawing Sheets

MICROCUTTING DEVICE AND INCISING METHOD

BACKGROUND OF THE INVENTION

1. Field of the Invention

The present invention relates to a microcutting device for cutting or incising a minute sample of organisms, such as egg cells and protozoa, and so forth under microscopic observation or the like; and a method of cutting or incising the minute sample using this device.

2. Related Background Art

Japanese Patent Application Laid-Open No. 8-85018 discloses a conventional microcutting device for cutting or incising a minute sample of organisms, such as egg cells and protozoa, and the like. This device is made of a thin film plate formed by use of a semiconductor manufacturing technique. Thus made microcutting device is sharper than a metal-blade incision device and is suitable for incising microorganism samples, while being capable of mass production.

SUMMARY OF THE INVENTION

In the microcutting device in accordance with the present invention, its blade has a cutting edge positioned outside the width of a support member which supports the blade. Consequently, the support member can be restrained from obstructing incision. Also, the blade, its cutting edge in particular, is provided with a heater. As a result, minute samples can be incised smoothly.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DETAILED DESCRIPTION OF THE PREFERRED EMBODIMENTS

In the following description, microcutting devices in accordance with embodiments of a present invention will be explained. Constituents identical to each other or having functions identical to each other will be referred to with numerals or letters identical to each other, without their overlapping explanations being repeated.

Figure 1A:
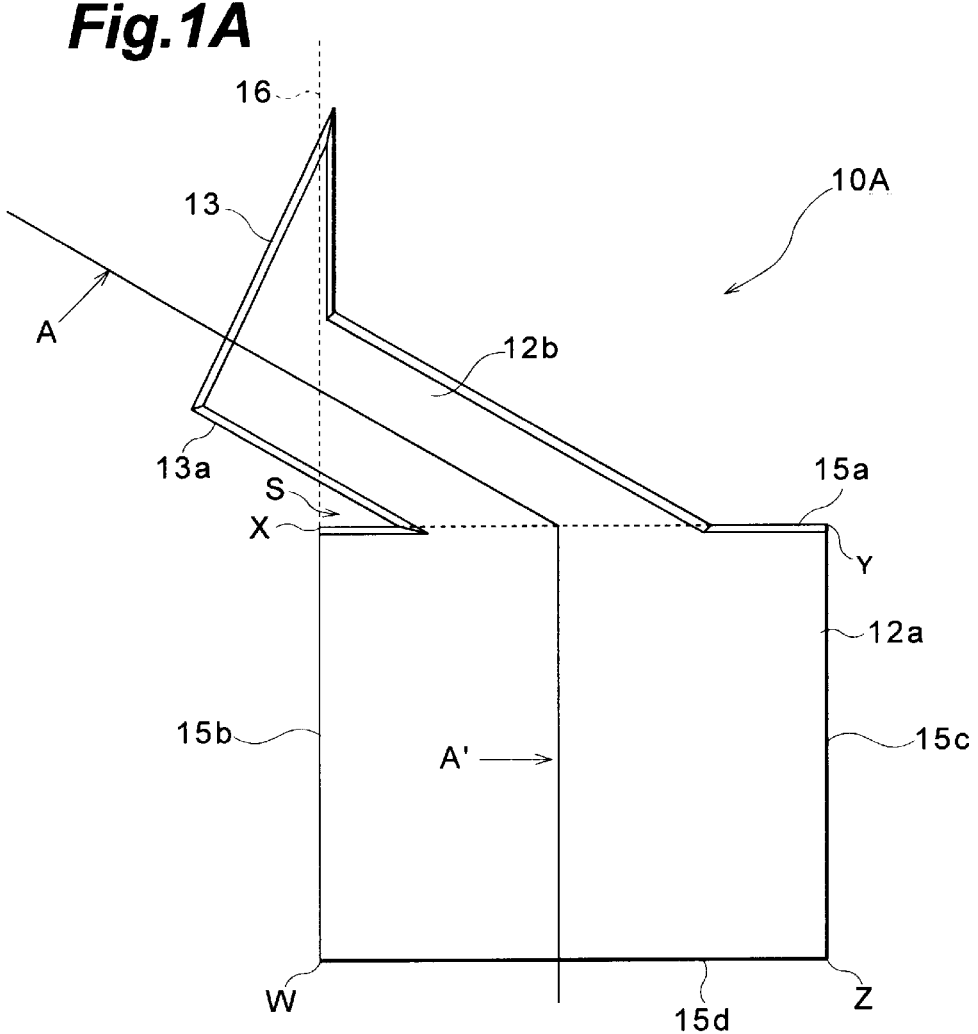
FIG. 1A is a plan view of a microcutting device 10A in accordance with a first embodiment.
Figure 1B:
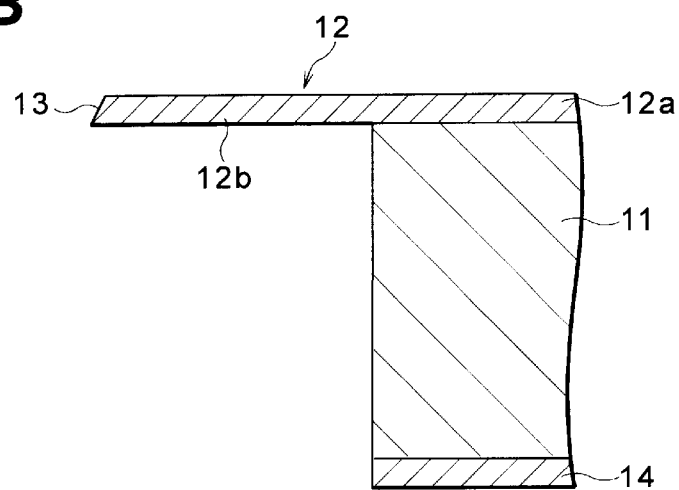
FIG. 1B is a sectional view of the device shown in FIG. 1A, taken along arrowed lines A–A'.

FIG. 1A is a plan view of a microcutting device 10A in accordance with a first embodiment; whereas FIG. 1B is a sectional view of the device shown in FIG. 1A, taken along arrowed lines A–A'.

The microcutting device 10A of this embodiment is formed by a semiconductor manufacturing technique which will be explained later. The microcutting device 10A comprises a support member 11 made of a silicon substrate, and a thin film plate 12 supported by and secured onto the surface of the support member 11. The surface of the support member 11 is rectangular. This rectangular surface is defined by a distal main ridge portion (line) 15a (line connecting apexes x and y), side ridge portions (lines) 15b (line connecting apexes w and x) and 15c (line connecting apexes y and z) respectively located on both sides of the main ridge portion 15a, and a proximal main ridge portion (line) 15d (line connecting apexes w and z). The width of the support member 11 is 1 to 2 mm.

Figure 2:
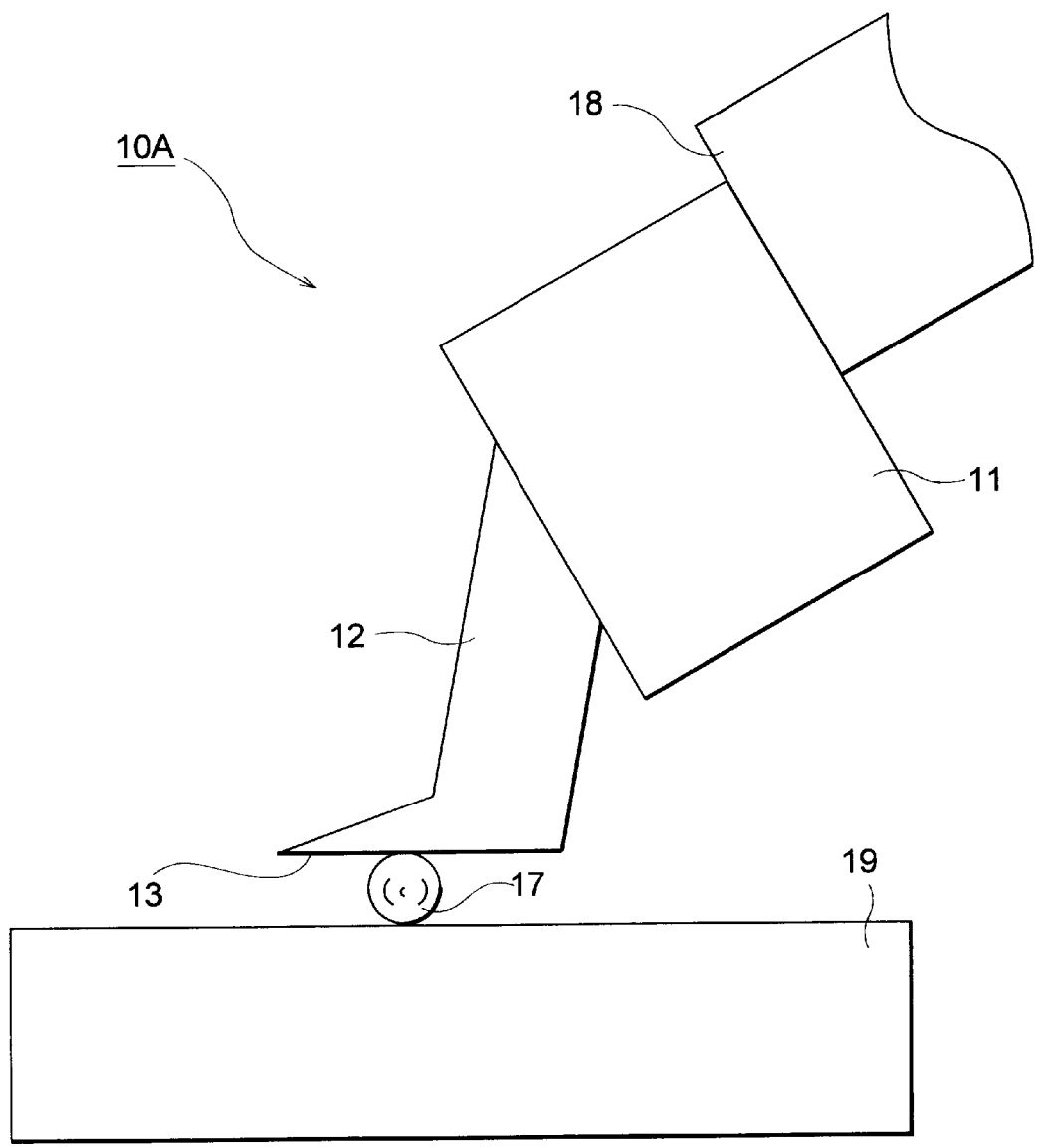
FIG. 2 is a view showing how a sea urchin egg 17 (having a diameter of 100 $\mu$m) is cut with the microcutting device 10A in accordance with the first embodiment.

The proximal side of the microcutting device 10A is connected to a manipulator (not depicted) by way of a holder 18 (see FIG. 2).

The thin film plate 12 is formed by patterning of a silicon nitride film. The thin film plate 12 has an attachment portion 12a secured to the support member 11, and a blade portion 12b extending from the attachment portion 12a. The blade portion 12b is shaped like a boot, exposing its rear side. A side ridge line 13 of the blade portion 12b forms a cutting edge.

The blade portion 12b of the thin film plate 12 projects outside an extension line 16 of one side ridge portion 15b defining its width, whereby at least 50% of the cutting edge 13 is located outside the extension line 16. Accordingly, when cutting and incising an object to be processed, the side ridge portions 15b and 15c do not become obstacles, whereby operability improves. The blade portion 12 has an opposing line 13a, which extends from a predetermined point of the distal main ridge line 15a and faces the distal main ridge line 15a. The opposing line 13a and the distal main ridge line 15a facing the same form an acute angle therebetween, whereby a space S cut inside the side ridge line 15b by tens to hundreds of $\mu$m is interposed between the blade portion 12b and the support member 11.

Figure 1C:
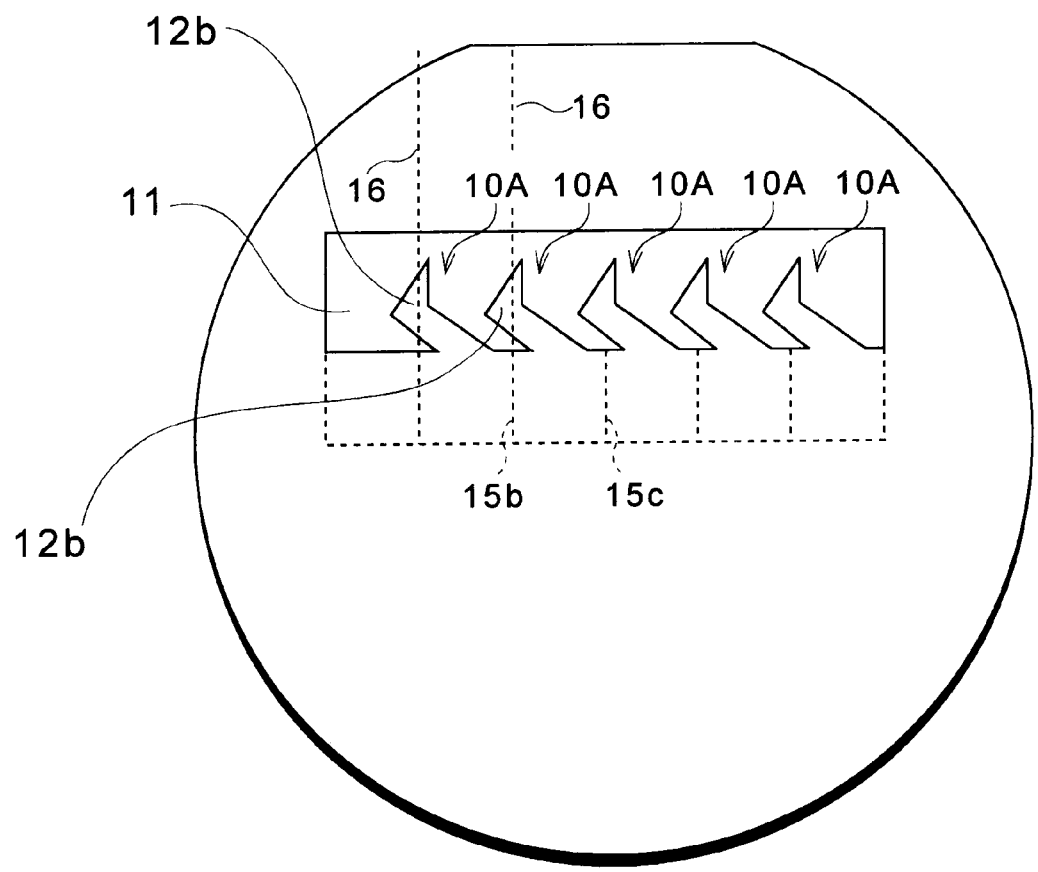
FIG. 1C is a plan view of a microcutting device array formed on a semiconductor wafer.

The space S functions as follows. Namely, in order to make this microcutting device 10A, as shown in FIG. 1C, a microcutting device array in which a plurality of pieces of microcutting devices 10A is cleaved and cut at the side ridge lines 15b and 15c, so as to separate the pieces of microcutting devices 10A from each other. In the case where the proximal end of the blade portion 12b of each thin film plate 12 is disposed on its corresponding extension line 16 while each blade portion 12b projects outside the extension line 16, a crack may enter into the blade portion 12b when each of the side ridge lines 15b and 15c between the devices is cleaved. Therefore, in the microcutting device 10A in accordance with this embodiment, the proximal end of the blade portion 12b is located at a position separated from the side ridge line 15b, thereby preventing the crack from entering therein. In other words, since the space S is located on the extension of the side ridge line 15b, the side ridge line 15b between the individual microcutting devices 10A can be cleaved and cut without applying stress to the blade portion 12b.

Disposed on the rear side of the support member 11 is a silicon nitride film 14 formed by patterning, which functions as a mask when etching the silicon substrate on the rear side of the blade portion 12b.

FIG. 2 is a view showing how a sea urchin egg 17 (having a diameter of 100 $\mu$) is cut with the microcutting device 10A in accordance with this embodiment. Upon cutting, the microcutting device 10A is secured to a tip of the holder 18 made of an aluminum rod, and the holder 18 is attached to a hydraulic manipulator (not depicted). The sea urchin egg 17 is placed on a slide glass 19. While the sea urchin egg 17 is observed through an inverted microscope MS, the cutting edge 13 of the microcutting device 10A is pressed against the sea urchin egg 17 from thereabove, and the manipulator is operated so as to move the cutting edge 13 in the longitudinal direction thereof, and the egg 17 is cut with the cutting edge 13 of the blade portion 12b by direct downward pressure with the horizontal back and forth motion. When this cutting operation was executed, the sea urchin egg 17 was easily cut without the support member 11 abutting against the slide glass 19, i.e., without the support member 11 obstructing the cutting operation. Thus, it has been found that the microcutting device 10A yields quite improved operability as compared with conventional microcutting devices.

Similar cutting operations were performed on a bovine ovum (having a diameter of 60 $\mu$m) and a mouse ovum (having a diameter of 30 $\mu$m). They could easily be cut as well.

In the following, with reference to FIGS. 3A to 3C, a method of making the microcutting device 10A in accordance with this embodiment will be explained.

Figure 3A:
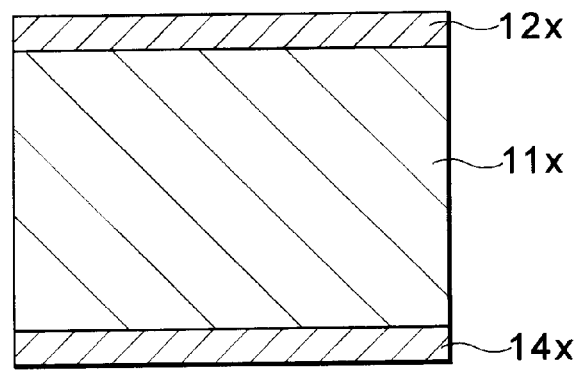
FIGS. 3A, 3B, and 3C are views for explaining a method of making the microcutting device 10A in accordance with the first embodiment.

First, as shown in FIG. 3A, a silicon substrate (Si) 11x with (100) surface azimuth having a thickness of 250 $\mu$m is prepared. On both sides of the substrate 11x, silicon nitride films (SiNx) 12x and 14x are respectively formed by use of low pressure chemical vapor deposition (LPCVD) technique, each with a thickness of 0.7 $\mu$m. Then, of the silicon nitride film 12x on the upper surface of the substrate 11x, the region to be formed with the thin film plate 12 is covered with a mask (not depicted) which is formed by photolithography technique, while exposing the remaining region. Also, of the silicon nitride film 14x on the lower surface of the substrate 11x, the region to be formed with the support member 11 is covered with a mask (not depicted) which is formed by photolithography technique, while exposing the remaining region. Though a part (attachment portion 12a) of the region to be formed with the thin film plate 12 faces the region to be formed with the support member 11, the remaining part (blade portion 12b) does not face the region to be formed with the support member 11.

Figure 3B:
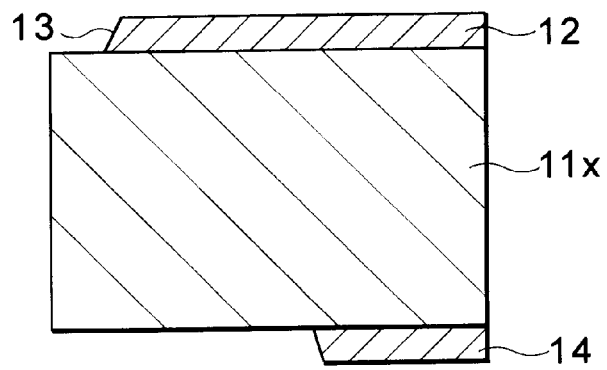

As shown in FIG. 3B, after these masks are formed, the exposed regions of the silicon nitride films 12x and 14x are dry-etched, thereby forming the upper and lower thin film plates 12 and 14. Dry etching for these patterning operations is effected by reactive ion etching (RIE). For this reactive ion etching process, a reactive ion etching apparatus is used. The etching gas used for reactive ion etching is a mixed gas composed of $SF_6$ and He. The pressure of the mixed gas is 0.24 torr, and the power applied thereto is 200 W. When reactive ion etching was performed under this condition, a sharp cutting edge 13 having a tapered cross-sectional form was obtained as shown in FIG. 3B.

Figure 3C:
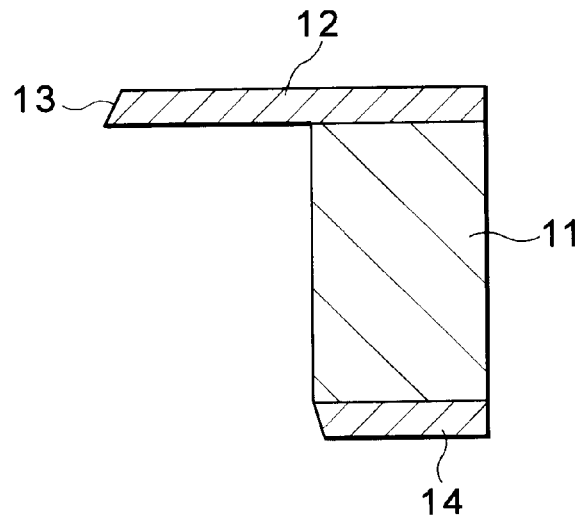

Thereafter, as shown in FIG. 3C, the exposed regions of the upper and lower surfaces of the substrate 11x are wet-etched. The etchant used in this wet etching process is an aqueous tetramethyl ammonium hydroxide (TMAH) solution. When the solution substrate 11x is immersed into the aqueous TMAH solution, since the crystal azimuth (111) surface has a dissolving rate much lower than that of the (100) surface, anisotropic etching progresses along the direction directed into the substrate 11x.

The aqueous TMAH solution does not dissolve the silicon nitride films 12 and 14. Accordingly, the silicon nitride films 12 and 14 function as etching masks when etching the silicon substrate 11x. When the temperature of TMAH is at 85° C., etching completes in about 320 minutes. Here, however, in order to completely eliminate unnecessary regions of the substrate 11x, wet etching is performed about 30 minutes (about 10%) longer. When wet etching was performed under this condition, silicon to become the support member 11 was left, whereby the microcutting device 10A shown in FIGS. 1A and 1B was completed.

Thus, since the microcutting device 10A in accordance with this embodiment can be made by use of a semiconductor manufacturing technique, such as the most established silicon process in particular, it becomes inexpensive and excellent. Further, as the photolithography mask for patterning the thin film (silicon nitride film in this embodiment) formed on the substrate is changed, the form of the thin film plate 12 can be easily altered.

Figure 4:
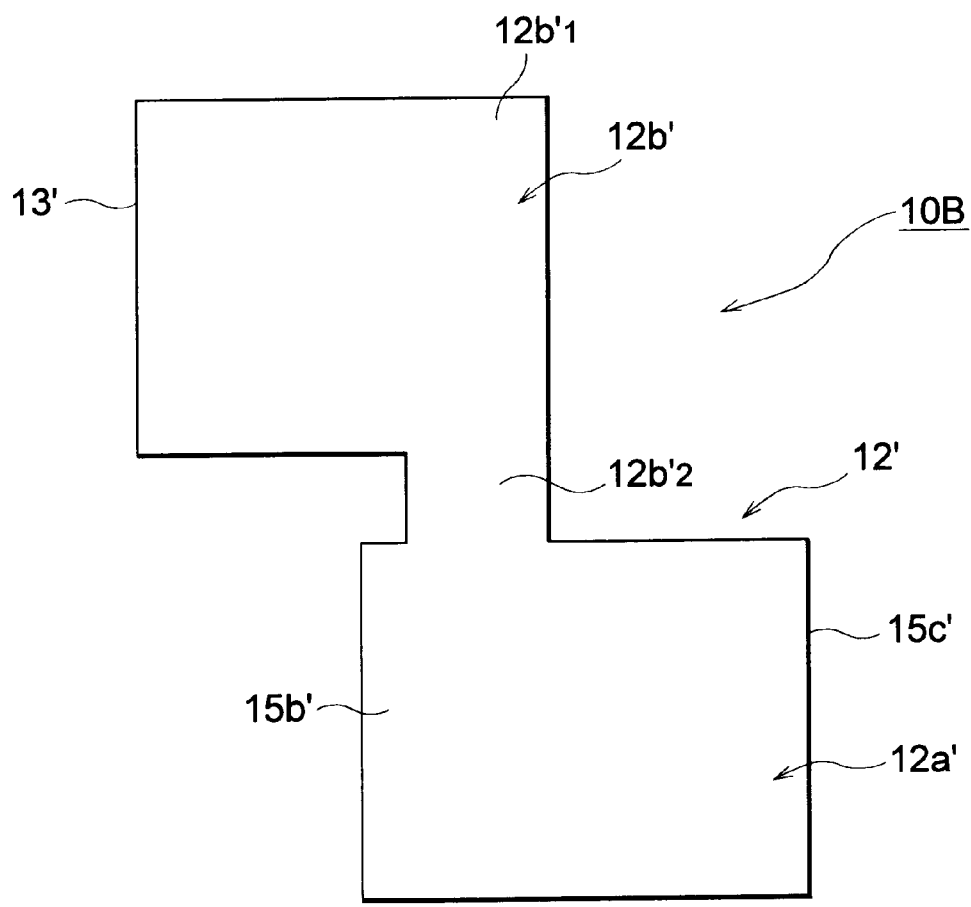
FIG. 4 is a plan view of a microcutting device 10B in accordance with a second embodiment.

FIG. 4 is a plan view of a microcutting device 10B in accordance with the second embodiment. The microcutting device 10B differs from the above-mentioned microcutting device 10A only in its form. Its thin film plate 12' has a blade portion 12b' projecting outside an extension line of one of side ridge portions 15b' and 15c' of its attachment portion 12a'. The blade portion 12b' comprises a rectangular region 12b$_1$' having a cutting edge 13' at one end thereof, and a joint region 12b$_2$' connecting the rectangular region 12b$_1$' and the attachment portion 12a' together.

Figure 5A:
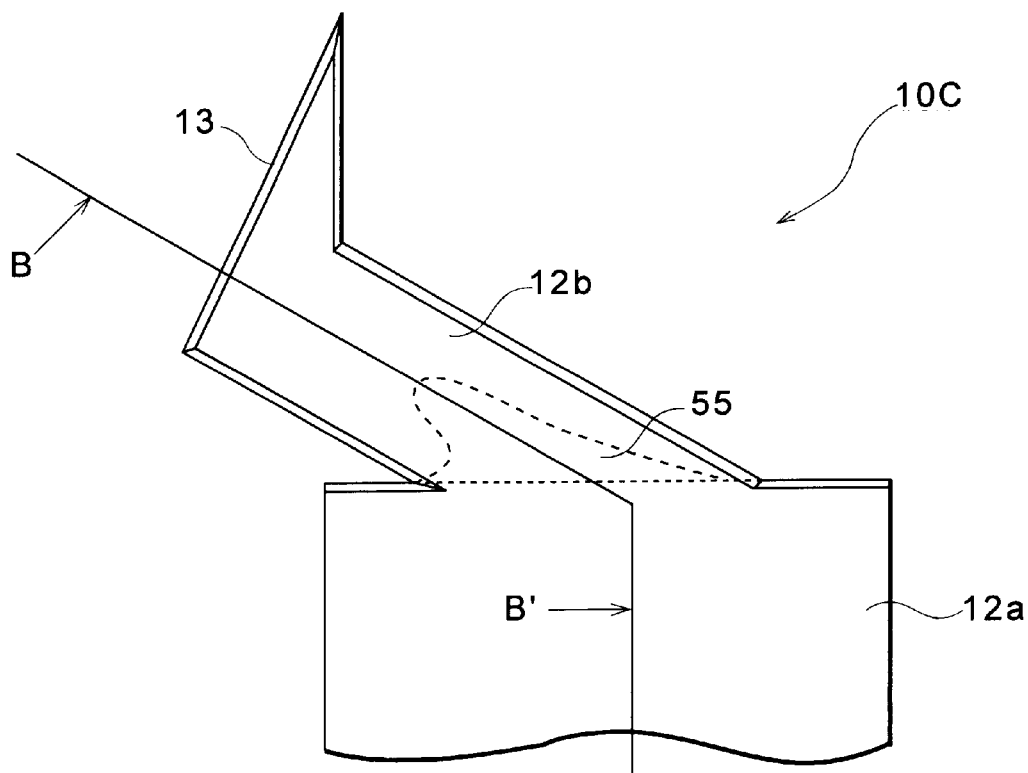
FIG. 5A is a plan view of a microcutting device 10C in accordance with a third embodiment.

FIG. 5A is a plan view of a microcutting device 10C in accordance with a third embodiment; whereas FIG. 5 is a sectional view of the device shown in FIG. 5A, taken along arrowed lines B–B'. Here, in the plan view, a reinforcement 55 is seen through. The microcutting device 10C in accordance with the third embodiment differs from the microcutting device 10A of the first embodiment only in that it further comprises a plate fortifying film 54 and the reinforcement 55.

Figure 5B:
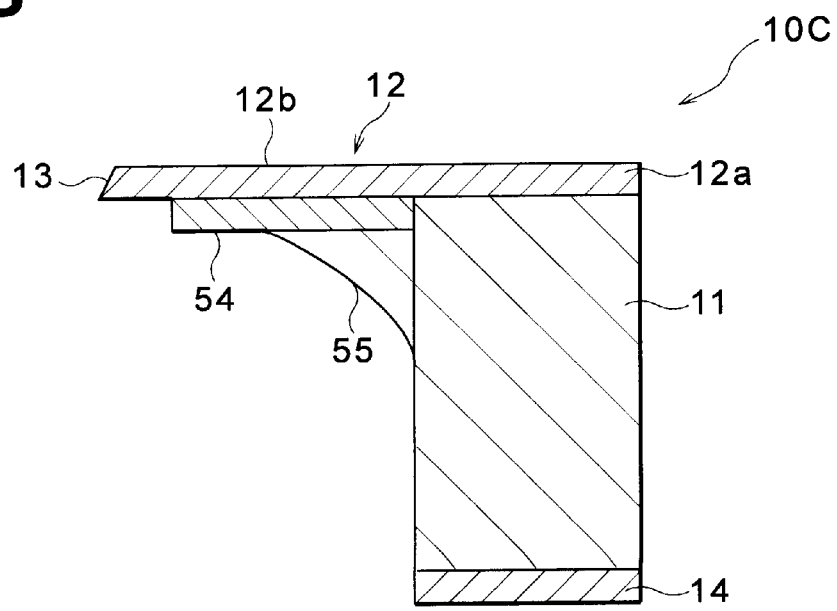
FIG. 5B is a sectional view of the device shown in FIG. 5A, taken along arrowed lines B–B'.

The plate fortifying film 54, which is formed by boron-doped silicon, is disposed on the rear surface (surface on the support member 11 side) of the blade portion 12b of the thin film plate 12. The plate fortifying film 54 is disposed on substantially the whole lower surface of the blade portion 12b of the thin film plater 12. Here, if the plate fortifying film 54 extends to the vicinity of the cutting edge 13, it may block the object from being cut and incised. Accordingly, as shown in FIG. 5B, the plate fortifying film 54 is separated from the cutting edge 13. The plate fortifying film 54 greatly improves the mechanical durability of the thin film plater 12, thereby enhancing that of the microcutting device 10C.

The reinforcement 55 extends from the root region of the thin film plate 12 toward the center of the thin film plate 12 and is formed by silicon. The reinforcement 55 is disposed at the root of the thin film plate 12 like a beam. Accordingly, the reinforcement 55 greatly improves the mechanical durability of the thin film plate 12, thereby enhancing the durability of the microcutting device 10C. The mechanical durability of the microcutting device 10C surely improves even when the reinforcement 55 is disposed at a part of the root region. It may also extend to the vicinity of the center of the thin film plate 12 as in the case of this embodiment, however. The film 54 and reinforcement 55 also improve the mechanical rigidity of the thin film plate 12, thereby making it possible to process objects having a high rigidity which have conventionally been incapable of being cut and incised.

In the following, a process of making the microcutting device 10C in accordance with this embodiment will be explained with reference to FIGS. 6A to 6D.

Figure 6A:
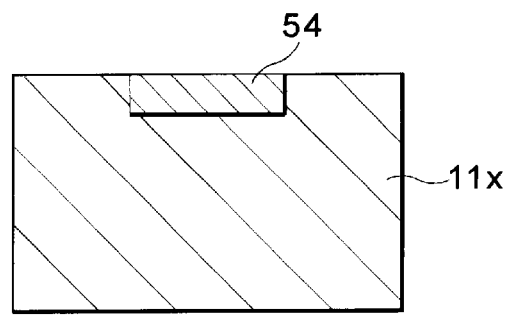
FIGS. 6A, 6B, 6C and 6D are views for explaining a method of making the microcutting device 10C in accordance with the third embodiment.

First, as shown in FIG. 6A, a silicon substrate 11x with (100) surface azimuth having a thickness of 250 μm is prepared. A thermal oxidation method based on a known silicon process is used for forming thermally oxidized silicon films (not depicted) on both surfaces of the substrate 11x. Then, photolithography technique is used for eliminating a part of the thermally oxidized silicon films so as to expose a region which will later become the plate fortifying film. While using the remaining part of the thermally oxidized silicon films as a mask, a known thermal diffusion method is used such that the silicon substrate 11x is doped with boron (B) (the latter being diffused into the former), thereby forming the boron-doped silicon film (plate fortifying film) 54 on the exposed surface of the substrate 11x. For diffusing boron, a solid-phase diffusion source including B is used. After the solid-phase diffusion source is placed on the substrate 11x, the latter is heat-treated for 30 minutes at 1,175° C. When diffusion was effected under this condition, the boron concentration of the boron-doped silicon film 54 became $2 \times 10^{20}/cm^3$ at a depth of 2 μm from the surface of the silicon substrate 11x. Thereafter, the thermally oxidized silicon films used as the mask are eliminated.

Figure 6B:
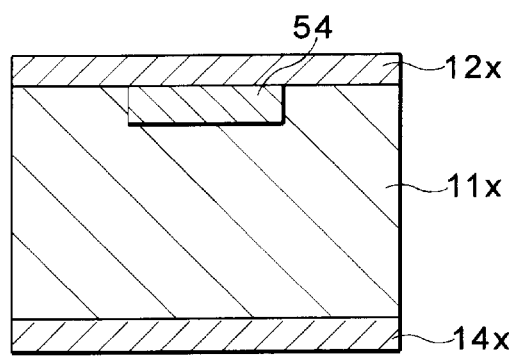

Then, as shown in FIG. 6B, on both sides of the substrate 11x, silicon nitride films (SiNx) 12x and 14x are respectively formed by use of low pressure chemical vapor deposition (LPCVD) technique, each with a thickness of 0.7 μm. Then, of the silicon nitride film 12x on the upper surface of the substrate 11x, the region to be formed with the thin film plate 12 is covered with a mask (not depicted) which is formed by photolithography technique, while exposing the remaining region. Also, of the silicon nitride film 14x on the lower surface of the substrate 11x, the region to be formed with the support member 11 is covered with a mask (not depicted) which is formed by photolithography technique, while exposing the remaining region. Though a part (attachment portion 12a) of the region to be formed with the thin film plate 12 faces the region to be formed with the support member 11, the remaining part (blade portion 12b) does not face the region to be formed with the support member 11.

Figure 6C:
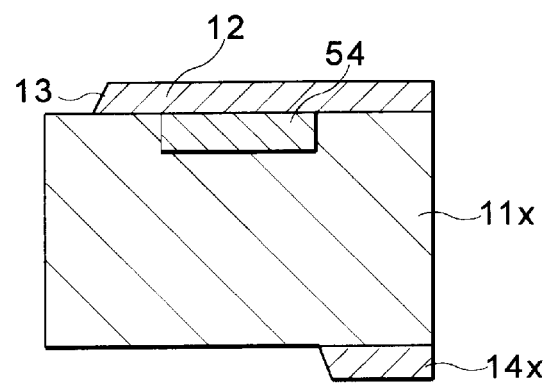

As shown in FIG. 6C, after these masks are formed, the exposed regions of the silicon nitride films 12x and 14x are dry-etched, thereby forming the upper and lower thin film plates 12 and 14. Dry etching for these patterning operations is effected by reactive ion etching (RIE). For this reactive ion etching process, a reactive ion etching apparatus is used. The etching gas used for reactive ion etching is a mixed gas composed of $SF_6$ and He. The pressure of the mixed gas is 0.24 torr, and the power applied thereto is 200 W. When reactive ion etching was performed under this condition, a sharp cutting edge 13 having a tapered cross-sectional form was obtained as shown in FIG. 6C. Here, the patterning of the upper surface of the substrate 11x is effected such that the silicon nitride film 12x in the part corresponding to the cutting edge 13 projects from the boron-doped silicon film 54 by on the order of 10 to 20 μm.

Figure 6D:
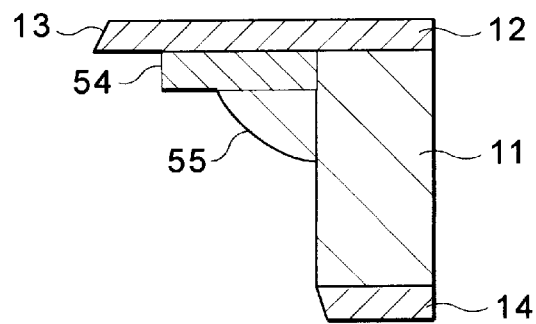

Thereafter, as shown in FIG. 6D, the exposed regions on the upper and lower surfaces of the substrate 11x are wet-etched. The etchant used in this wet etching process is an aqueous potassium hydroxide (KOH) solution. When the silicon substrate 11x is immersed into the aqueous potassium hydroxide (KOH) solution, as with the aqueous tetramethyl ammonium hydroxide (TMAH) solution, since the crystal azimuth (111) surface has a dissolving rate much lower than that of the (100) surface, anisotropic etching progresses. The aqueous potassium hydroxide (KOH) solution does not dissolve the silicon nitride films 12 and 14. Accordingly, the silicon nitride films 12 and 14 function as etching masks when etching the silicon substrate 11x. The dissolving rate of the boron-doped silicon film 54 with respect to the aqueous potassium hydroxide (KOH) solution is much lower than that of the silicon substrate 11x not doped with boron. Consequently, boron-doped silicon remains in the lower surface of the silicon nitride film 12, thereby forming the plate fortifying film 54. When the silicon substrate 11x is etched for about 100 minutes while the temperature of KOH is at 85° C., it attains a just-etching state. Here, however, in order to form the reinforcement 55, the etching condition is set to an under etching state (at 90 minutes) by about 10 minutes (about 10%). When wet etching was performed under this condition, together with the support member 11, the reinforcement 55 was formed near the root of the thin film plate 12 like a beam, whereby the microcutting device 10C in accordance with this embodiment was completed.

Thus, since the microcutting device 10C in accordance with this embodiment uses a silicon process, it becomes inexpensive and excellent. Also, since the reinforcement 55 is disposed, the mechanical durability of the thin film plate 12 greatly improves, thereby enhancing the durability of the microcutting device 10C. Further, the plate fortifying film 54 improves the mechanical durability and mechanical rigidity of the thin film plate 12, thereby making it possible to process objects having a high rigidity which have conventionally been incapable of being cut and incised.

Figure 7:
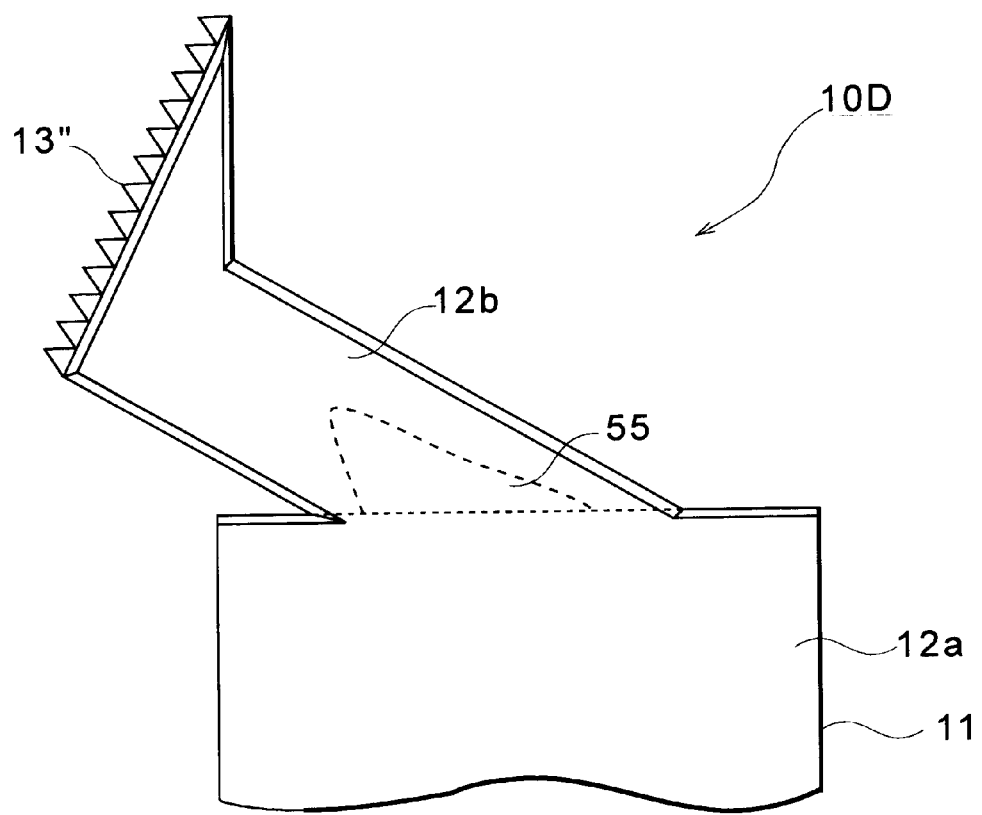
FIG. 7 is a plan view of a microcutting device 10D in accordance with a fourth embodiment.

FIG. 7 is a plan view of a microcutting device 10D in accordance with a fourth embodiment. Here, its reinforcement 55 is seen through. This microcutting device 10D differs from the microcutting device 10C of the third embodiment only in the form of its cutting edge. The thin film plate 12 supported by the support member 11 has a cutting edge 13" which is saw-toothed. When the cutting edge 13 of the microcutting device 10C shown in FIGS. 5A and 5B is pressed against a minute object to be processed, the object to be processed may slide away from the cutting edge 13. Such a phenomenon can be prevented by this embodiment since the cutting edge 13" is saw-toothed. In this embodiment, as with the third embodiment, the microcutting device 10D comprises a plate fortifying film 54 and the reinforcement 55. However, the cutting edge 13" may also be saw-toothed while the microcutting device 10D is provided with neither plate fortifying film nor reinforcement.

Figure 8A:
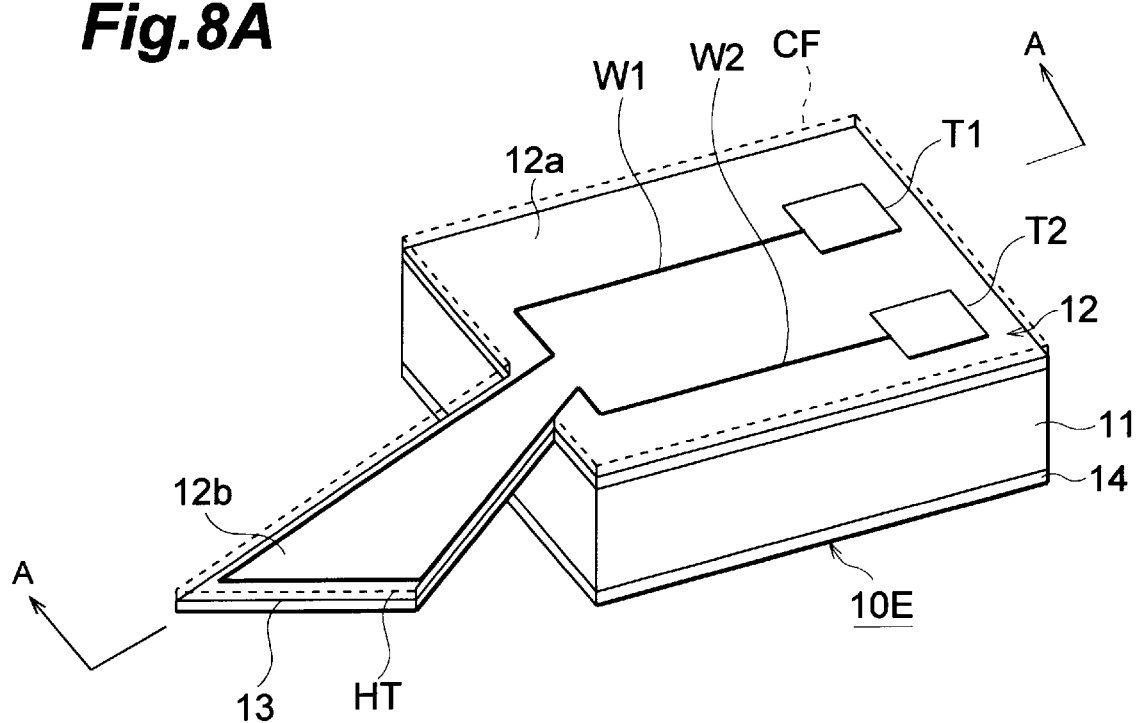
FIG. 8A is a plan view of a microcutting device 10E in accordance with a fifth embodiment.
Figure 8B:
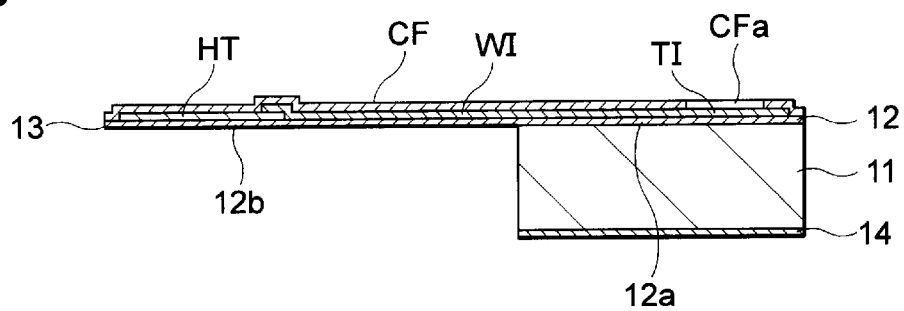
FIG. 8B is a sectional view of the device shown in FIG. 8A, taken along arrowed lines A–A'.

FIG. 8A is a perspective view of a microcutting device 10E in accordance with a fifth embodiment; whereas FIG. 8B is a sectional view of the device shown in FIG. 8A, taken along arrowed lines A–A'. This microcutting device 10E is identical to the microcutting device 10A of the first embodiment except that it further comprises a heater HT, wires W1 and W2, terminals (pads) T1 and T2, and a coated insulating film CF; and that its blade portion 12b is formed like a quadrangle instead of a pentagon.

Namely, the microcutting device 10E comprises a support member 11, and a thin film plate 12 supported by and secured onto the surface of the support member 11; whereas the thin film plate 12 has an attachment portion 12a secured to the support member 11, and a blade portion 12b extending from the attachment portion 12a. The blade portion 12b has a side ridge line 13 which forms a cutting edge.

The thin-film like heater HT, the wires W1 and W2, and the terminals T1 and T2 are disposed on the thin film plate 12. Specifically, the thin film heater HT is constituted by a material such as nichrome, which generates Joule heat when current is supplied thereto, and is disposed along the cutting edge 13 on the blade portion 12b in the vicinity of the cutting edge 13. The terminals T1 and T2 are constituted by a material, such as a metal, which has a resitivity lower than that of the thin film heater HT. Here, the heater HT may also be made of the same conductive material as that of the wires W1 and W2, e.g., low-resistance conductive material such as gold. In this case, the line width of the heater HT is narrowed so as to increase its resistance value. Since the blade portion 12b has a relatively low thermal resistance, the heater HT may be attached to the support member 11 as well.

The terminals T1 and T2 are disposed on the attachment portion 12a; whereas the wires W1 and W2 respectively extend from the terminals T1 and T2 so as to crawl over the thin film plate 12 and electrically connect with both end portions of the thin film heater HT. The coated insulating film CF, which is made of silicon nitride, is formed on the thin film plate 12 so as to cover the heater HT and the wires W1 and W2. Namely, the coated insulating film CF is a protective film and prevents the heater HT and the wires W1 and W2 from deteriorating, breaking, and so forth. Namely, even in the case where the microcutting device 10E is immersed in a physiological solution such as synthetic seawater, the wires W1 and W2 and the heater HT doe not come into contact with the solution, whereby electric power transfer efficiency can be prevented from decreasing due to corrosion of these elements and the physiological solution. Here, the coated insulating film CF has two opening (contact holes) CFa respectively positioned on the terminals T1 and T2, thereby exposing the surfaces of the terminals T1 and T2.

When current is supplied from the terminals T1 and T2 to the heater HT through the wires W1 and W2, the blade portion 12b, such as its cutting edge 13 in particular, is heated by the Joule heat generated by the heater HT. Consequently, upon incising a minute biological sample, a portion of the skin of the minute sample (e.g., outer coat of an egg cell) which comes into contact with the cutting edge 13 is heated. Therefore, while the binding of the cell is being broken, the cell can be smoothly cut from the beginning of cutting. Also, the stress applied to the blade portion 12b upon cutting can be reduced, thus allowing the durability of the microcutting device 10E to improve. Further, since the heater HT of the microcutting device 10E is made of a thin film, it is advantageous in that cutting is not obstructed thereby.

Here, the total thickness of the blade portion 12b and thin film heater HT is 0.8 $\mu$m, the length of the cutting edge 13 is 430 $\mu$m, and the distance from the cutting edge 13 to the support member 11 is 550 $\mu$m.

In the following, a method of making the microcutting device 10E in accordance with this embodiment will be explained with reference to FIGS. 9A to 9E.

Figure 9A:
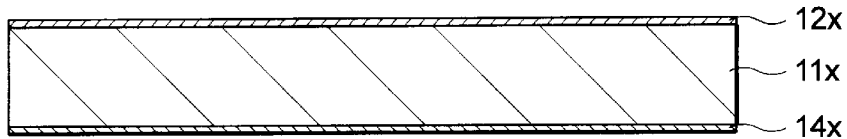
FIGS. 9A, 9B, 9C, 9D, and 9E are views for explaining a method of making the microcutting device 10E in accordance with the fifth embodiment.

First, as shown in FIG. 9A, a silicon substrate (Si) 11x with (100) surface azimuth having a thickness of 250 $\mu$m is prepared. On both sides of the substrate 11x, silicon nitride films (SiNx) 12x and 14x are respectively formed by use of low pressure chemical vapor deposition (LPCVD) technique, each with a thickness of 0.7 $\mu$m. Then, of the silicon nitride film 12x on the upper surface of the substrate 11x, the region to be formed with the thin film plate 12 is covered with a mask (not depicted) which is formed by photolithography technique, while exposing the remaining region. Also, of the silicon nitride film 14x on the lower surface of the substrate 11x, the region to be formed with the support member 11 is covered with a mask (not depicted) which is formed by photolithography technique, while exposing the remaining region. Though a part (attachment portion 12a) of the region to be formed with the thin film plate 12 faces the region to be formed with the support member 11, the remaining part (blade portion 12b) does not face the region to be formed with the support member 11.

Figure 9B:
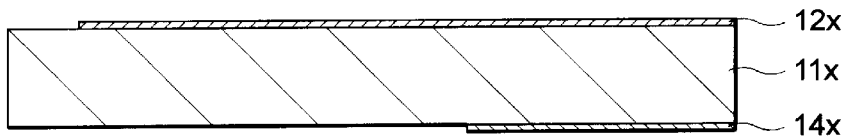

As shown in FIG. 9B, after these masks are formed, the exposed regions of the silicon nitride films 12x and 14x are dry-etched, thereby forming the upper and lower thin film plates 12 and 14. Dry etching for these patterning operations is effected by reactive ion etching (RIE). For this reactive ion etching process, a reactive ion etching apparatus is used. The etching gas used for reactive ion etching is a mixed gas composed of $SF_6$ and He. The pressure of the mixed gas is 0.24 torr, and the power applied thereto is 200 W.

Figure 9C:
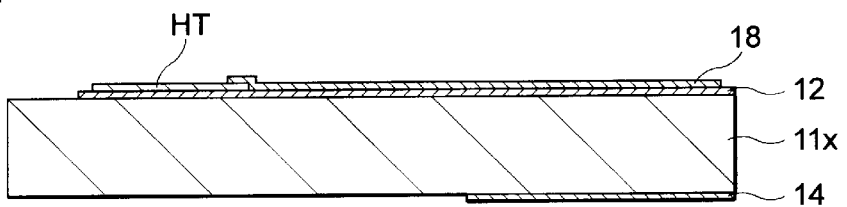

Thereafter, as shown in FIG. 9C, lift-off technique is used for forming a nichrome thin film HT, gold thin film wires W1 and W2, and gold pads T1 and T2 on the silicon nitride film 12, each with a thickness of 0.1 $\mu$m, by patterning.

Figure 9D:
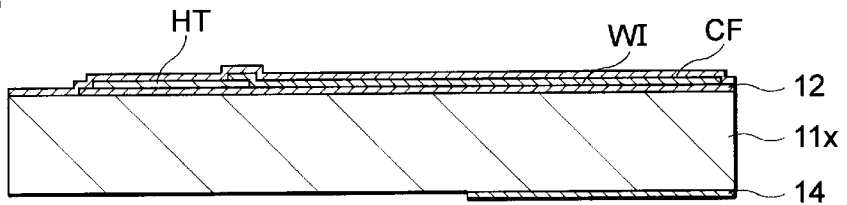

Subsequently, as shown in FIG. 9D, a silicon nitride film CF having a thickness of 0.1 $\mu$m is formed on the silicon nitride film 12.

Figure 9E:
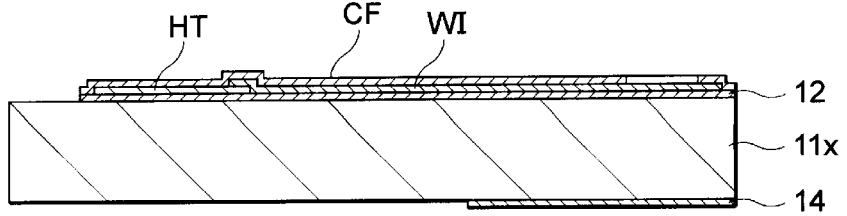

Then, as shown in FIG. 9E, the silicon nitride films CF and 12 are patterned by use of dry etching technique in conformity to the forms of the support member 11 and contact holes CFa.

Finally, the exposed regions on the upper and lower surfaces of the substrate 11x are wet-etched. The etchant used in this wet-etching process is an aqueous tetramethyl ammonium hydroxide (TMAH) solution or aqueous potassium hydroxide (KOH) solution. When wet-etching is performed under this condition, silicon to become the support member 11 is left, thereby completing the microcutting device 10E shown in FIGS. 8A and 8B.

Figure 10:
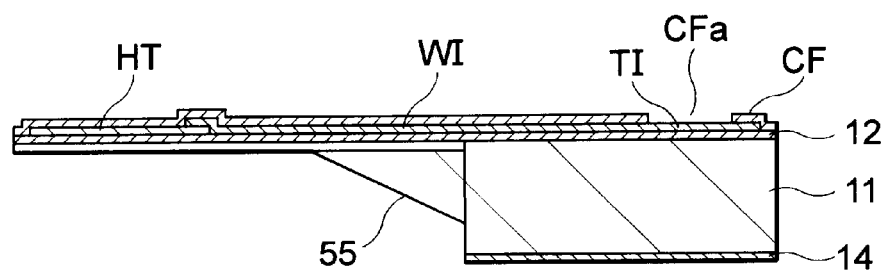
FIG. 10 is a perspective view of a microcutting device 10F in accordance with a sixth embodiment.

FIG. 10 is a sectional view of a microcutting device 10F in accordance with a sixth embodiment. This microcutting device 10F is identical to the microcutting device 10C of the third embodiment except that, as with the microcutting device 10E of the fifth embodiment, it further comprises a heater HT, wires W1 and W2, terminals (pads) T1 and T2, and a coated insulating film CF, and that its blade portion 12b is formed like a quadrangle instead of a pentagon.

Figure 11:
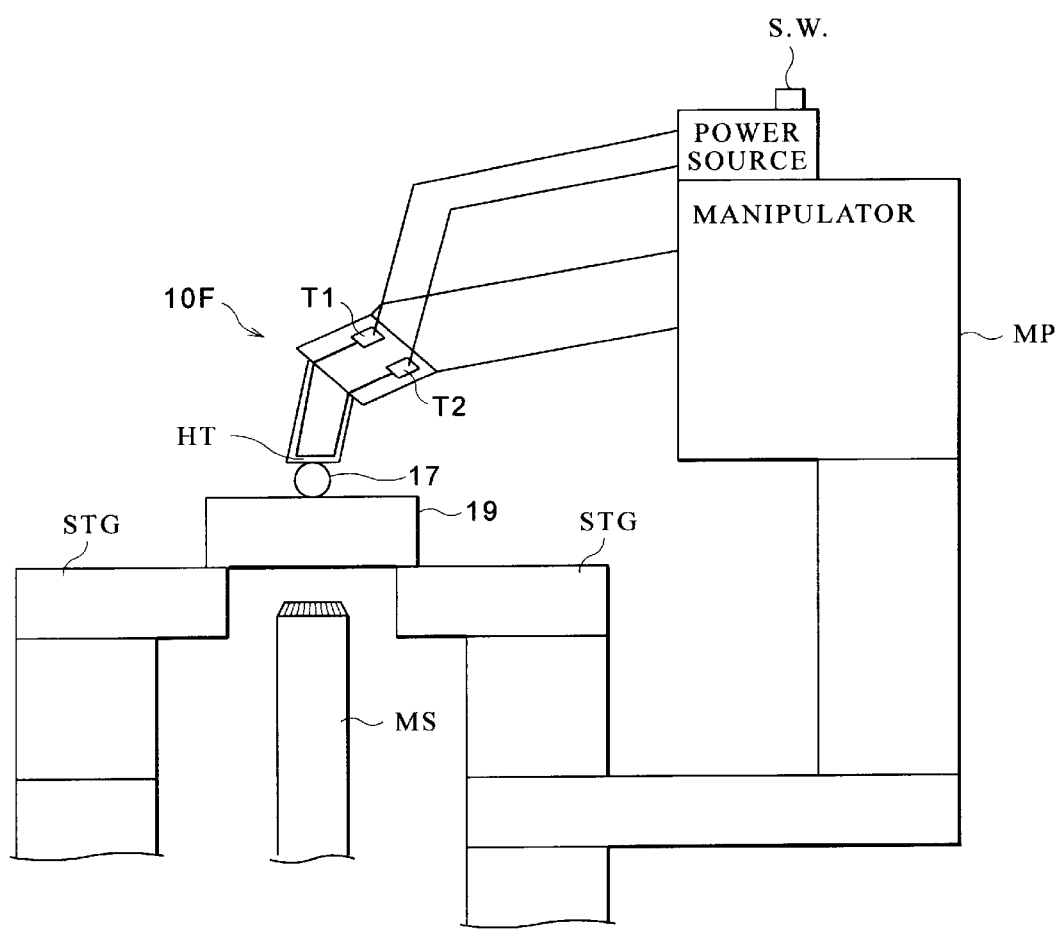
FIG. 11 is a view of an incising apparatus equipped with the microcutting device 10F.

FIG. 11 shows an incising apparatus equipped with the microcutting device 10F. This apparatus comprises a slidable stage STG, an inverted microscope MS for observing a sample 17 placed on a slide glass 19 on the stage STG, and a manipulator MP for moving a holder which holds the microcutting device 10F. The terminals T1 and T2 of the microcutting device 10F are electrically connected to a power source of the incising apparatus. When a switch SW of the power source is turned on, electric power is supplied to the heater HT so as to heat the latter.

Figure 12:
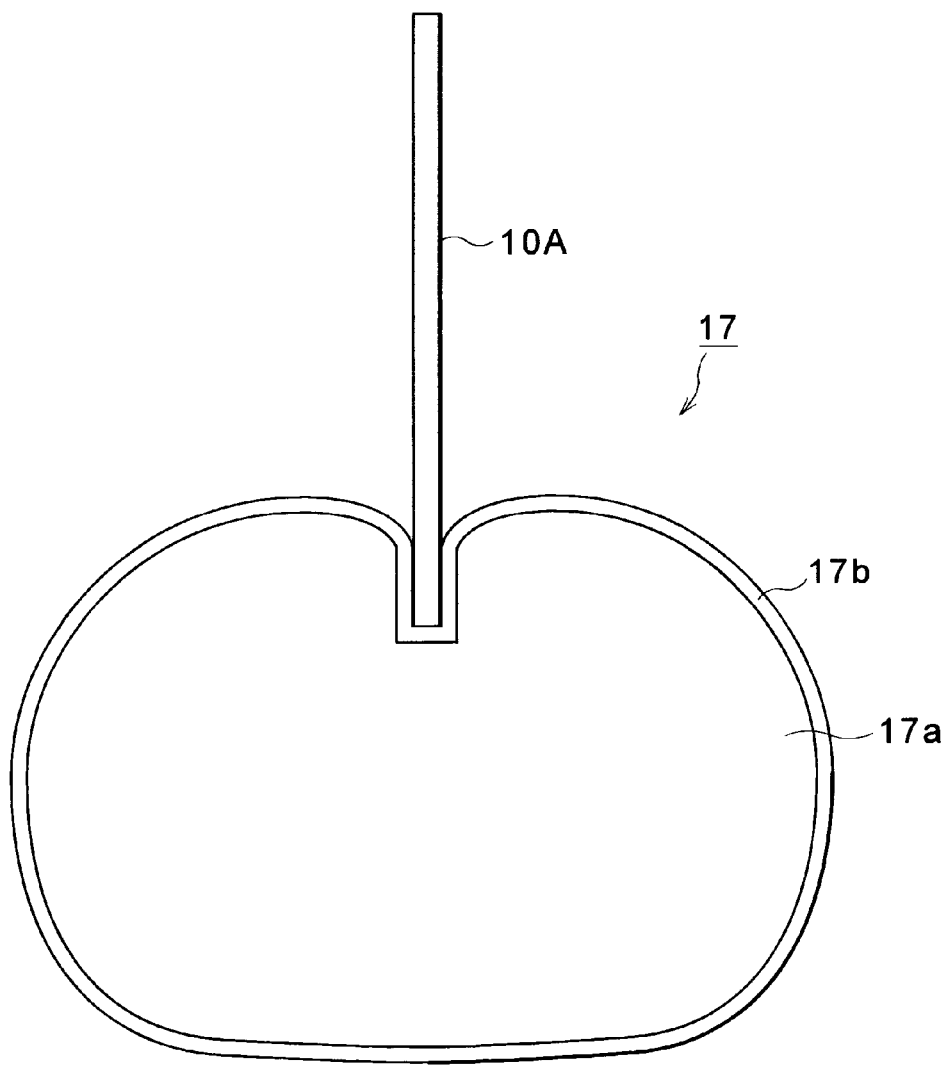
FIG. 12 is a view showing the sample 17 and the microcutting device 10A without a heater HT.

FIG. 12 is a view showing the sample 17 and the microcutting device 10A without the heater HT. The sample 17 is a minute organism sample, such as egg cell, protozoa, or nerve cell, comprising jelly-like contents and a skin or nerve cell, comprising jelly-like contents and a skin covering and protecting the contents. In the case where the sample 17 is an egg cell, it has a jelly-like inner protoplasm 17a and a cell coat 17b covering the inner protoplasm 17a. When the microcutting device 10A without the heater HT is used for cutting the egg cell 17; the egg cell 17 is placed under a physiological solution such as synthetic seawater, and the cutting edge 13 of the microcutting device 10A is pressed against the egg cell 17 so as to cut the latter. In the case where the microcutting device is not equipped with a heater, while its operability becomes excellent since the blade portion is disposed outside the width of the support member as mentioned above, the egg cell 17 may deform greatly as depicted.

By contrast, in the case of the microcutting device 10F, since its cutting edge 13 is heated, the portion of the cell coat 17b in contact with the cutting edge 13 is heated. Accordingly, while the binding of the cell is being broken, the cell can be cut smoothly from the beginning of cutting, whereby the egg cell 17 can be restrained from deforming.

In the following, a cutting or incising method using the above-mentioned microcutting device 10F will be explained.

First, the microcutting device 10F is attached to the three-dimensional manipulator MP shown in FIG. 11. Here, the microcutting device 10F is placed under the microscope MS. Without supplying current to the heater HT to heat the same, the manipulator MP is driven such that the cutting edge 13 comes into contact with a portion of the egg cell 17 to be cut. Thereafter, current is supplied to the heater HT to heat the same, and the manipulator MP is driven so as to move the blade portion 12b along the longitudinal direction of the cutting edge 13. Consequently, the skin 17b of the sample is melted to cut off by heat. Accordingly, from the beginning of cutting, the egg cell 17 can be cut smoothly with a small force, whereby the egg cell 17 can be restrained from deforming.

Here, after being heated prior to cutting, the heater HT is continuously heated till only the part of the skin 17b initially in contact therewith upon cutting is cut or incised. After this part is incised, heating is stopped. Alternatively, after being heated prior to cutting, the heater HT may be continuously heated till the cutting or incising operation throughout the egg cell 17 is completed. In other words, current may be supplied to the heater HT either instantaneously only at the beginning, or continuously or intermittently from the start of current supply to the end of cutting. In this method, at the point of time when the cutting edge is positioned to be in contact with the sample surface, the heater HT is not heated. Accordingly, at this point of time, even when the sample 17 is placed in a physiological solution or the like, no cavitation (bubble) occurs around the microcutting device 10F. Namely, since bubbles which may obstruct observation through the microscope MS do not occur upon positioning, the operator can easily position the microcutting device 10F while observing the sample 17 through the microscope MS. Here, the heater HT may also be heated prior to positioning.

The microcutting device 10F was manufactured. The resistance value of the heater HT of the microcutting device 10F was about 50 $\Omega$. Thus manufactured microcutting device 10F was used for cutting a sea urchin ovum having a diameter of 100 $\mu$m placed in seawater. Cutting was performed in the following manner. First, without supplying electricity to the heater HT, the blade portion 12b was positioned such that its cutting edge 13 cam into contact with the sea urchin ovum. Thereafter, a pulsed voltage of 5 V (with a pulse width of about 100 msec) was applied to the terminals T1 and T2 of the microcutting device 10F, thereby instantaneously raising the temperature of the heater HT and blade portion 12b. The temperature of the cutting edge 13 at this time was about 200° C. At the same time when the application of pulsed voltage was started, the blade portion 12b was moved along the longitudinal direction of the cutting edge 13. Consequently, even at the beginning of cutting, the sea urchin ovum was prevented from greatly deforming whereby the sea urchin could be cut with a cutting force which is about 1/10 that in the case with no heating. Here, there was no damage to the blade portion 12b.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A microcutting device comprising:
   (a) a support member made of a semiconductor material, the support member having a side ridge line that extends in a length direction; and
   (b) a thin film plate disposed on said support member, said thin film plate including a blade portion extending from said support member in the length direction, at least a part of said blade portion being disposed outside of the side ridge line that extends in the length direction.

2. A microcutting device according to claim 1, wherein said blade portion has a proximal end positioned inside an extension line of the side ridge line of said support member.

3. A microcutting device according to claim 1, wherein said blade portion includes a cutting edge having a tapered cross section in a thickness direction thereof.

4. A microcutting device according to claim 1, wherein said blade portion includes a saw-toothed cutting edge.

5. A microcutting device according to claim 1, wherein said thin film plate is made of an insulator.

6. A microcutting device according to claim 1, wherein said semiconductor material is silicon.

7. A microcutting device according to claim 6, wherein said thin film plate is made of silicon nitride.

8. A microcutting device according to claim 1, further comprising a reinforcement disposed between a surface of said blade portion on said support member side and said support member.

9. A microcutting device according to claim 1, further comprising a plate fortifying film disposed on a surface of said blade portion on said support member side.

10. A microcutting device according to claim 1, further comprising a heater attached to said blade portion.

11. An incising apparatus comprising:
the microcutting device according to claim 1;
a microscope for observing said microcutting device; and
a manipulator for moving said microcutting device.

12. A incising method comprising the steps of:
(a) moving a microcutting device on a sample without heating;
(b) heating said microcutting device while said microcutting device is in contact with said sample; and
(c) moving said microcutting device in contact with said sample relative to said sample.

13. An incising method comprising the steps of:
(a) moving a microcutting device on a sample without heating;
(b) heating said microcutting device while said microcutting device is in contact with said sample;
(c) moving said microcutting device in contact with said sample relative to said sample; and
(d) observing said microcutting device in operation by a microscope.

* * * * *